United States Patent
Kim et al.

(10) Patent No.: US 8,624,026 B2
(45) Date of Patent: Jan. 7, 2014

(54) METHOD OF PREPARING SITAGLIPTIN AND INTERMEDIATES USED THEREIN

(75) Inventors: Nam Du Kim, Hwaseong-si (KR); Ji Yeon Chang, Seoul (KR); Dong Jun Kim, Osan-si (KR); Hyun Seung Lee, Seoul (KR); Jae Hyuk Jung, Goyang-si (KR); Young Kil Chang, Seoul (KR); Gwan Sun Lee, Seoul (KR)

(73) Assignee: Hanmi Science Co., Ltd, Hwaseong-Si (KR)

( * ) Notice: Subject to any disclaimer, the term of this patent is extended or adjusted under 35 U.S.C. 154(b) by 0 days.

(21) Appl. No.: 13/502,260

(22) PCT Filed: Oct. 19, 2010

(86) PCT No.: PCT/KR2010/007150
§ 371 (c)(1),
(2), (4) Date: Apr. 16, 2012

(87) PCT Pub. No.: WO2011/049344
PCT Pub. Date: Apr. 28, 2011

(65) Prior Publication Data
US 2012/0214997 A1 Aug. 23, 2012

(30) Foreign Application Priority Data
Oct. 21, 2009 (KR) .......................... 10-2009-0100336

(51) Int. Cl.
*C07D 487/00* (2006.01)
(52) U.S. Cl.
USPC ........................................................ 544/350
(58) Field of Classification Search
USPC ........................................................ 544/350
See application file for complete search history.

(56) References Cited

FOREIGN PATENT DOCUMENTS

| EP | 2 397 141 A1 | 12/2011 |
|---|---|---|
| WO | 2004/085378 A1 | 10/2004 |
| WO | 2004/085661 A2 | 10/2004 |
| WO | 2004/087650 A2 | 10/2004 |
| WO | 2009/084024 A2 | 7/2009 |
| WO | 2009/085990 A2 | 7/2009 |
| WO | 2010/122578 A2 | 10/2010 |

OTHER PUBLICATIONS

Ahn et al., "Synthesis, Biological Evaluation and Structural Determination of β-aminoacyl-containing Cyclic Hydrazine Derivatives as Dipeptidyl Peptidase IV (DPP-IV) Inhibitors," Bioorganic & Medicinal Chemistry Letters, 2007, vol. 17, pp. 2622-2628.
Naidu et al., "A Simple and Efficient Approach to 1,3-aminoalcohols: Application to the Synthesis of (+)-negamycin," Tetrahedron Letters, 2007, vol. 48, pp. 3793-3796.
Zeng et al., "A Practical Synthesis of Trifluorophenyl R-amino Acid: the Key Precursor for the New Anti-Diabetic Drug Sitagliptin," Chinese Chemical Letters, 2009, vol. 20, pp. 1397-1399.
Hansen et al., "Highly Efficient Asymmetric Synthesis of Sitagliptin," J. Am. Chem. Soc., 2009, vol. 131, pp. 8798-8804.
Hansen et al., "First Generation Process for the Preparation of the DPP-IV Inhibitor Sitagliptin," Organic Process Research & Development, 2005, vol. 9, No. 5, pp. 634-639.
European Patent Office, European Search Report issued in corresponding EP Application No. 10825169.5, dated Apr. 24, 2013.
Taiwanese Patent Office, Taiwanese Office Action issued in corresponding TW Application No. 99135733, dated May 30, 2013.

*Primary Examiner* — Douglas M Willis
(74) *Attorney, Agent, or Firm* — Sughrue Mion, PLLC

(57) ABSTRACT

Disclosed are a novel, simple and low-cost method for preparing sitagliptin of formula (I), as DPP-IV (dipeptidyl peptidase IV) inhibitor, which is useful in treating type 2 diabetes mellitus and key intermediates used in said preparation of sitagliptin:

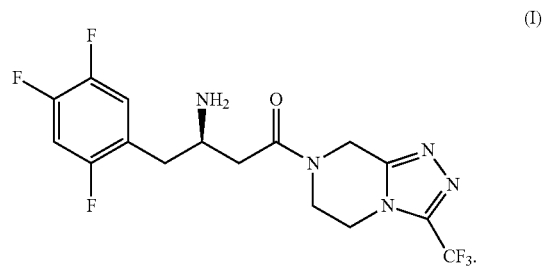

(I)

6 Claims, No Drawings

METHOD OF PREPARING SITAGLIPTIN AND INTERMEDIATES USED THEREIN

FIELD OF THE INVENTION

The present invention relates to a novel method of preparing sitagliptin, and intermediates used therein.

BACKGROUND OF THE INVENTION

Sitagliptin phosphate is a selective inhibitor of the second generation dipeptidyl peptidase IV (DPP-4) and used to maintain the systemic concentration of incretin hormone at an optimum level. Sitagliptin phosphate monohydrate was approved in October 2006 by the US Food and Drug Administration (FDA) as an adjuvant in dietetics or kinesiatrics for treatment of patients with type-2 diabetes and it is marketed in the United States and Korea under the trade name of JANUVIA™ (as a single agent).

Various methods for preparing sitagliptin and sitagliptin phosphate have been developed. For example, International Patent Publication WO 2003/004498 discloses a method of introducing a chiral-amine group using a chiral pyrazine derivative and to prepare sitagliptin by Arndt-Eistert Homologation using t-butoxylcarbonylamino-4-(2,4,5-trifluorophenyl)-butyric acid as a sitagliptin intermediate, as shown in Reaction Scheme 1.

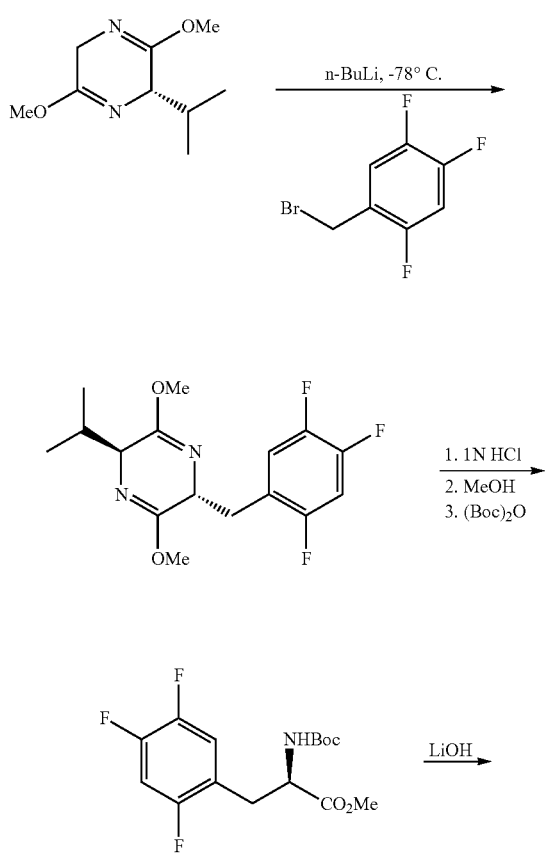

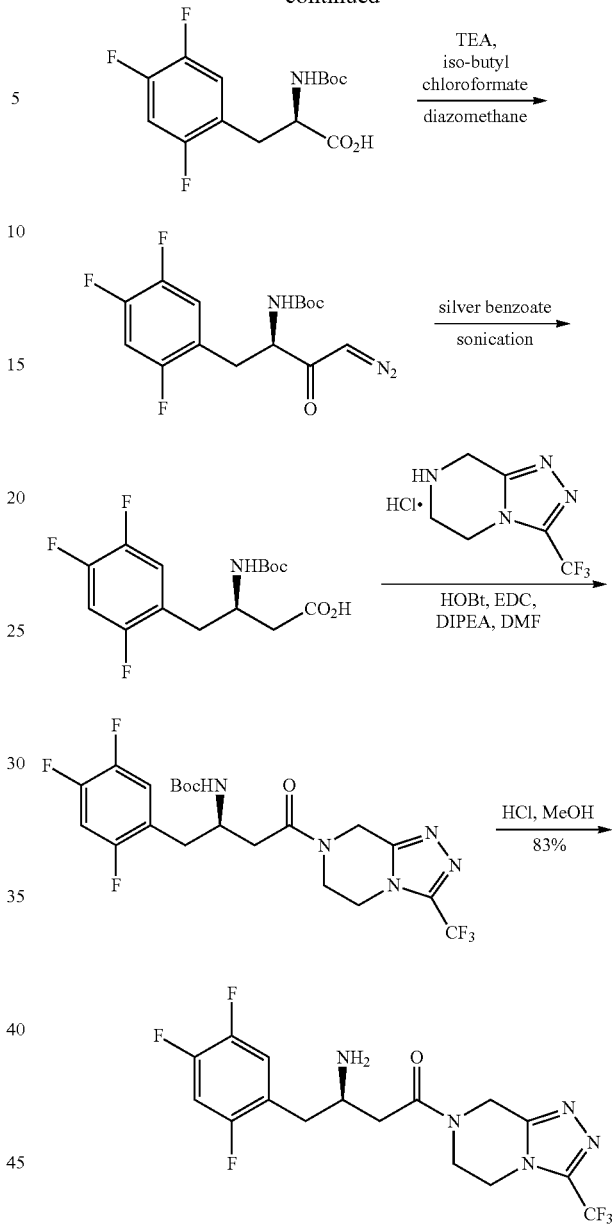

Wherein,

Boc is tert-butoxycarbonyl, TEA is trimethylamine, HOBt is 1-hydroxybenzotriazole, EDC is N-ethyl-N'-(3-dimethylaminopropyl)carbodiimide, and DIPEA is N,N-diisopropylethylamine.

International Patent Publication WO 2004/087650 discloses a method for preparing sitagliptin phosphate comprising the steps of: subjecting (2,4,5-trifluorophenyl)acetic acid to two-step reactions to obtain methyl 4-(2,4,5-trifluorophenyl)-3-oxophenylbutylate; conducting a stereoselective reduction of the resulting compound in the presence of (S)-BINAP-RuCl$_2$.Et$_3$N under a high hydrogen pressure; hydrolyzing the reduced product to obtain (3S)-3-hydroxy-4-(2,4,5-trifluorophenyl)-butyric acid, a key sitagliptin intermediate; and subjecting (3S)-3-hydroxy-4-(2,4,5-trifluorophenyl)-butyric acid to seven-step processes to obtain sitagliptin phosphate, as shown in Reaction Scheme 2.

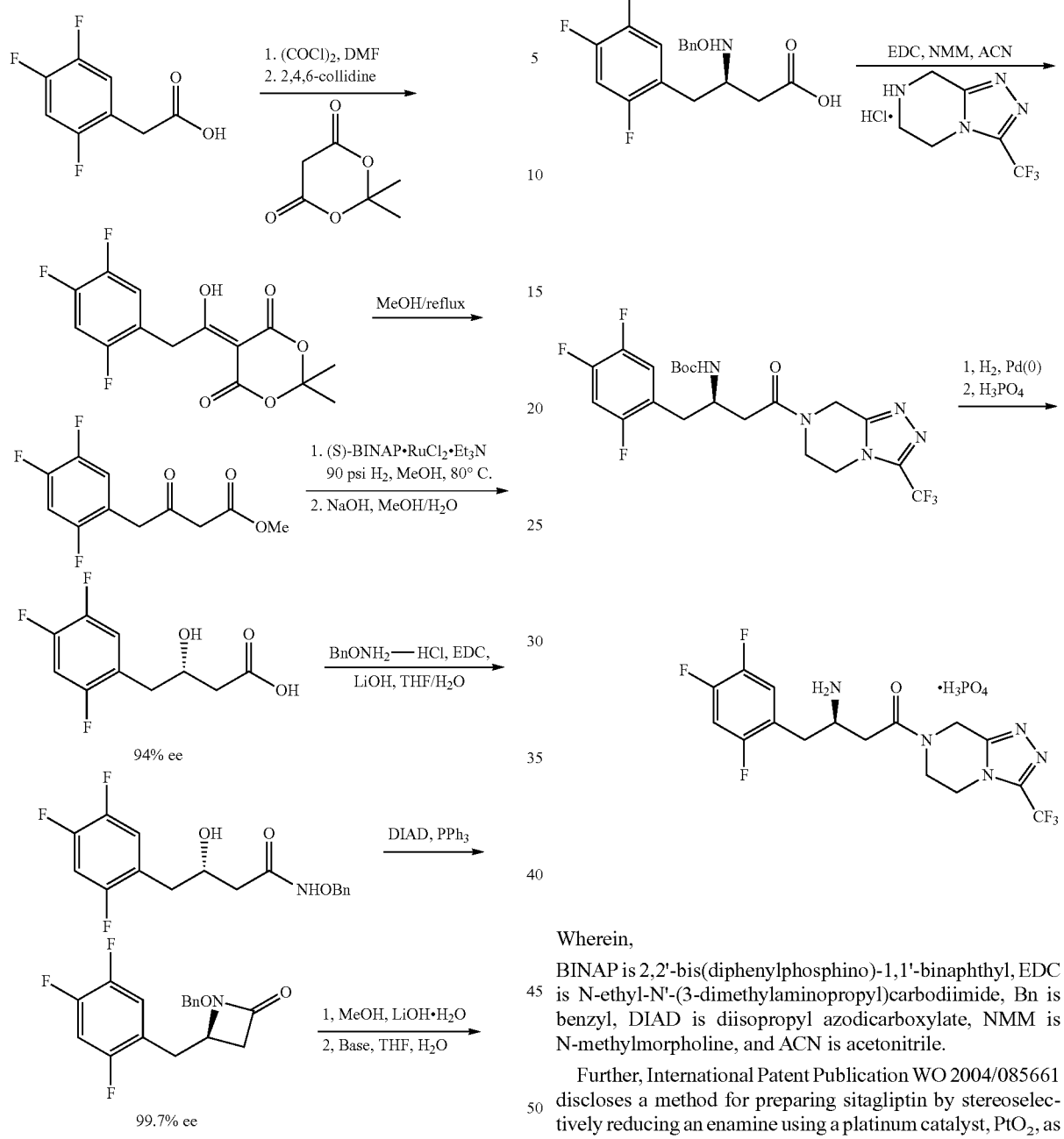

Wherein,

BINAP is 2,2'-bis(diphenylphosphino)-1,1'-binaphthyl, EDC is N-ethyl-N'-(3-dimethylaminopropyl)carbodiimide, Bn is benzyl, DIAD is diisopropyl azodicarboxylate, NMM is N-methylmorpholine, and ACN is acetonitrile.

Further, International Patent Publication WO 2004/085661 discloses a method for preparing sitagliptin by stereoselectively reducing an enamine using a platinum catalyst, $PtO_2$, as shown in Reaction Scheme 3.

Reaction Scheme 3

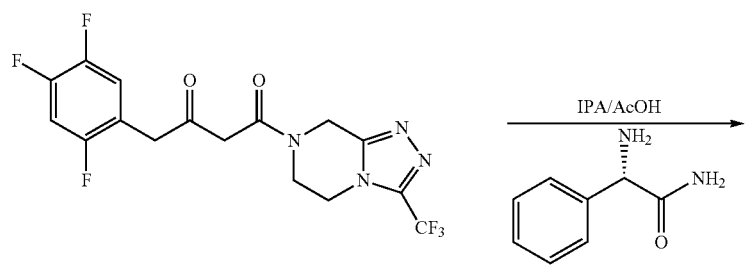

-continued

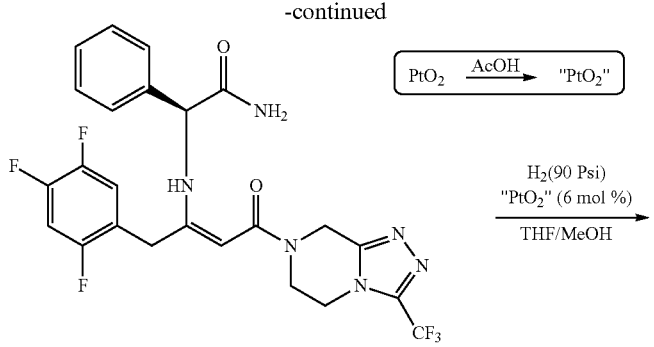

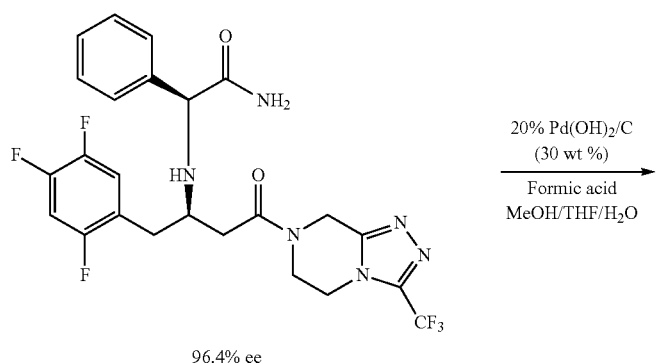

96.4% ee

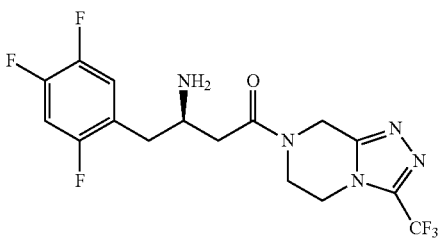

97% ee

Further, WO 2005/097733 discloses a method for preparing sitagliptin by stereoselectively reducing an enamine employing a rhodium-based catalyst, [Rh(cod)Cl]$_2$ having a chiral diphosphine ligand, as shown in Reaction Scheme 4.

Reaction Scheme 4

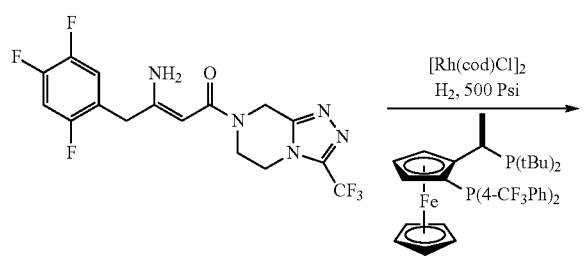

-continued

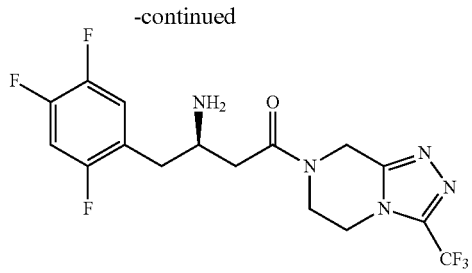

98% ee

The document [*J. Am. Chem. Soc.*, 2009, 131, p. 11316-11317] discloses a method for preparing sitagliptin by stereoselectively reducing an enamine using a ruthenium-based catalyst, Ru(OAc)$_2$ having a chiral diphosphine ligand, and International Patent Publication WO 2009/064476 discloses a method for preparing sitagliptin by stereoselectively reducing an enamine using Ru(OAc)$_2$ and a chiral diphosphine ligand, or using a chiral acid together with a borohydride reducing agent (e.g., NaBH$_4$).

The present inventors have endeavored to develop an improved method for preparing sitagliptin using a novel intermediate, and unexpectedly found that sitagliptin can be prepared by a simple and low-cost method using a chiral oxirane prepared from the commercially available epichlorohydrin.

SUMMARY OF THE INVENTION

Accordingly, it is an object of the present invention to provide a novel method of preparing sitagliptin and an intermediate used therein.

In accordance with one aspect of the present invention, there is provided a method of preparing sitagliptin of formula (I), which comprises the steps of:

(i) allowing (S)-epichlorohydrin to undergo arylation, epoxidation, and vinylation reactions to obtain (2R)-1-(2,4,5-trifluorophenyl)-4-pentene-2-ol of formula (II);

(ii) activating the hydroxyl group of the compound of formula (II) to conduct azidation to obtain (2S)-1-(2-azido-4-pentenyl)-2,4,5-trifluorobenzene of formula (III);

(iii) oxidizing the compound of formula (III) to obtain (3R)-3-azido-4-(2,4,5-trifluorophenyl)-butyric acid of formula (IV);

(iv) subjecting the compound of formula (IV) to a condensation reaction with a triazol derivative of formula (VI) to obtain (3R)-3-azido-1-(3-trifluoromethyl)-5,6-dihydro-8H-[1,2,4]triazolo[4,3-a]pyrazin-7-yl)-4-(2,4,5-trifluorophenyl)-butan-1-one of formula (V); and (v) reducing the azido group of the compound of formula (V):

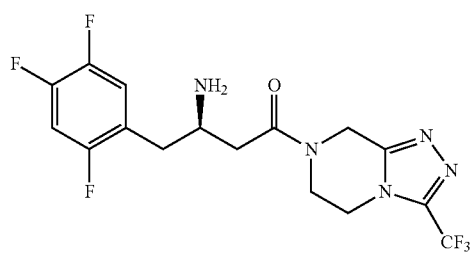 [SMILES: N[C@@H](CC(=O)N1CCn2c(nnc2C(F)(F)F)C1)Cc1cc(F)c(F)cc1F]

(I)

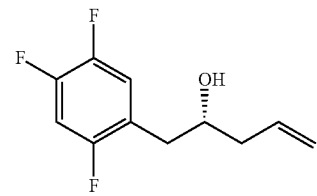

(II)

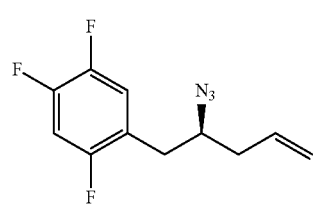

(III)

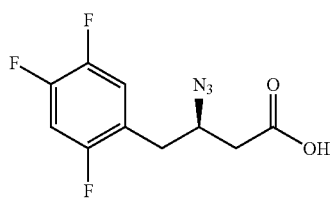

(IV)

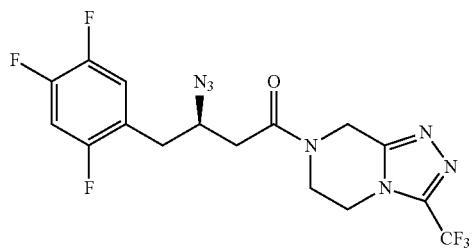

(V)

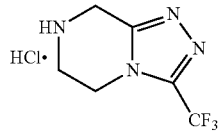

(VI)

In accordance with another aspect of the present invention, there is provided a compound of formula (II) which can be used as an intermediate in preparing the sitagliptin of formula (I):

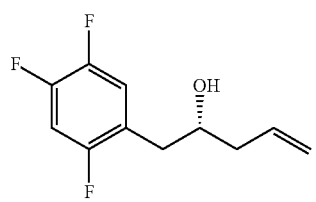

(II)

In accordance with a further aspect of the present invention, there is provided a compound of formula (III) which can be used as an intermediate in preparing the sitagliptin of formula (I):

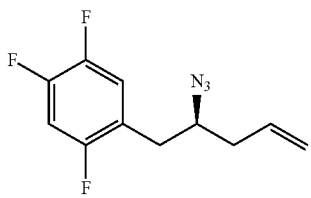

(III)

In accordance with a still further aspect of the present invention, there is provided a compound of formula (IV) which can be used as an intermediate in preparing the sitagliptin of formula (I):

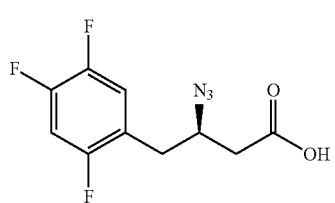

(IV)

In accordance with a still further aspect of the present invention, there is provided a compound of formula (V) which can be used as an intermediate in preparing the sitagliptin of formula (I):

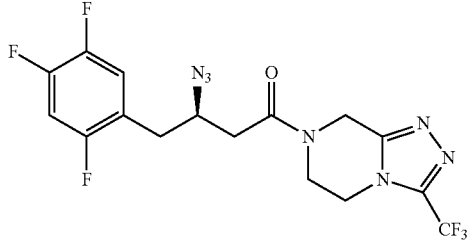

(V)

DETAILED DESCRIPTION OF THE INVENTION

Hereinafter, the present invention will be given in detail.

The method of preparing sitagliptin according to the present invention is characterized by the use of chiral oxirane, which has commercially available (S) or (R) isomer form in order to prepare the sitagliptin at a low cost.

The present invention provides the method of preparing sitagliptin which comprises the steps of:

(i) allowing (S)-epichlorohydrin to undergo arylation, epoxidation, and vinylation reactions to obtain (2R)-1-(2,4,5-trifluorophenyl)-4-pentene-2-ol of formula (II);

(ii) activating the hydroxyl group of the compound of formula (II) to conduct azidation to obtain (2S)-1-(2-azido-4-pentenyl)-2,4,5-trifluorobenzene of formula (III);

(iii) oxidizing the compound of formula (III) to obtain (3R)-3-azido-4-(2,4,5-trifluorophenyl)-butyric acid of formula (IV);

(iv) subjecting the compound of formula (IV) to a condensation reaction with a triazol derivative of formula (VI) to obtain (3R)-3-azido-1-(3-trifluoromethyl)-5,6-dihydro-8H-[1,2,4]triazolo[4,3-a]pyrazin-7-yl)-4-(2,4,5-trifluorophenyl)-butan-1-one of formula (V); and (v) reducing the azido group of the compound of formula (V).

Sitagliptin of formula (I) of the present invention may be prepared by the procedure shown in Reaction Scheme 5.

Reaction Scheme 5

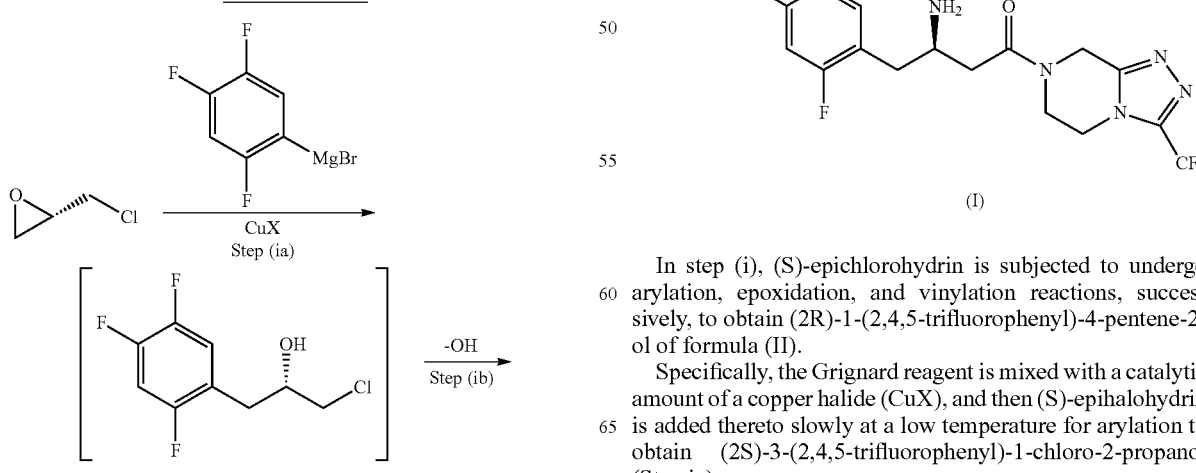

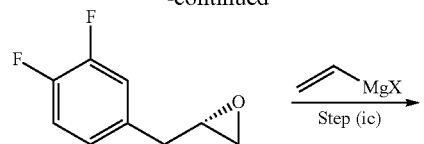

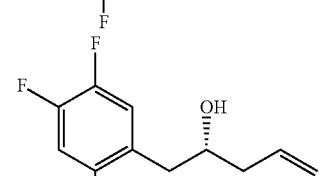

(II)

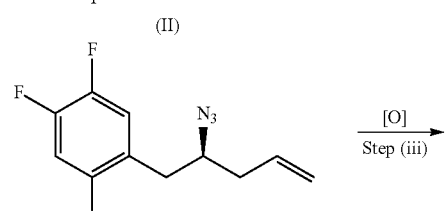

(III)

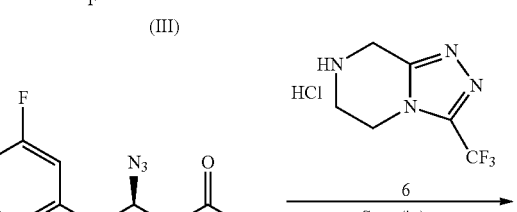

(IV)

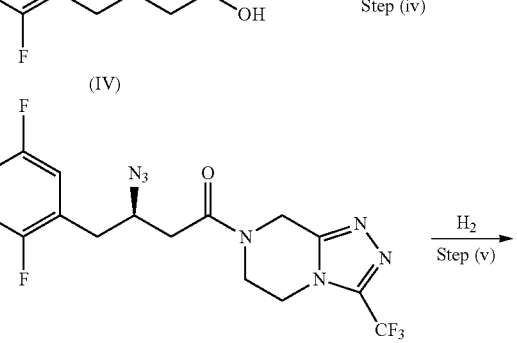

(V)

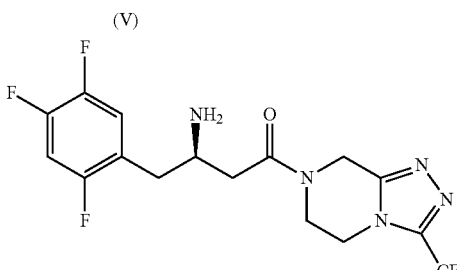

(I)

In step (i), (S)-epichlorohydrin is subjected to undergo arylation, epoxidation, and vinylation reactions, successively, to obtain (2R)-1-(2,4,5-trifluorophenyl)-4-pentene-2-ol of formula (II).

Specifically, the Grignard reagent is mixed with a catalytic amount of a copper halide (CuX), and then (S)-epihalohydrin is added thereto slowly at a low temperature for arylation to obtain (2S)-3-(2,4,5-trifluorophenyl)-1-chloro-2-propanol (Step ia).

The Grignard reagent may be prepared by treating 2,4,5-trifluorobenzene halide with magnesium (Mg) and organic halide alkyl (e.g., 1,2-dibromoethane); Mg and I₂; or isopropyl magnesium chloride (i-PrMgCl).

The 2,4,5-trifluorobenzene halide may be selected from the group consisting of 2,4,5-trifluorobenzene bromide, 2,4,5-trifluorobenzene chloride, and a mixture thereof.

The oxirane such as (S)-epichlorohydrin comprises (S) or (R) isomer, which is commercially available.

The copper halide may be selected from the group consisting of CuI, CuBr, CuBrS(CH₃)₂, and a mixture thereof.

Then, (2S)-3-(2,4,5-trifluorophenyl)-1-chloro-2-propanol thus obtained is dissolved in a solvent and subjected to an epoxylation reaction by adding strong base, to obtain (2S)-2-(2,4,5-trifluorobenzyl)-oxirane (Step ib).

The solvent used in this reaction may be tetrahydrofuran, diethyl ether and the like.

The strong base used in this reaction may be an alkali metal hydroxide such as sodium hydroxide, potassium hydroxide, lithium hydroxide, and a mixture thereof, and preferably, sodium hydroxide.

(2S)-2-(2,4,5-trifluorobenzyl)-oxirane thus obtained subjected to a vinylation reaction using vinylmagnesium halide in the presence of a catalytic amount of copper halide to selectively introduce the vinyl group at the terminal position, to obtain (2R)-1-(2,4,5-trifluorophenyl)-4-penten-2-ol of formula (II) (Step ic).

The copper halide may be selected from the group consisting of CuI, CuBr, CuBrS(CH₃)₂, and a mixture thereof.

The vinylmagnesium halide may be selected from the group consisting of vinylmagnesium bromide, vinylmagnesium chloride, and a mixture thereof.

The reaction carried out in a solvent such as tetrahydrofuran, diethyl ether and the like.

In step (ii), (2R)-1-(2,4,5-trifluorophenyl)-4-penten-2-ol of formula (II) obtained in step (i) is reacted with an activator having methansulfonyl or tosyl group to activate the hydroxyl group. Then, the resulting compound may be conducted to azidation for introducing the azido group to obtain (2S)-1-(2-azido-4-pentenyl)-2,4,5-trifluorobenzene of formula (III).

The activator used in this reaction may be selected form the group consisting of mesyl chloride, p-tosyl chloride, benzenesulfonyl chloride, trifluoromethansulfonyl chloride, and a mixture thereof which has methansulfonyl or tosyl group.

The azidation is conducted using a compound having the azido group such as sodium azide, preferably.

In step (iii), (2S)-1-(2-azido-4-pentenyl)-2,4,5-trifluorobenzene of formula (III) obtained in step (ii) is allowed to oxidize the alkenyl group of the compound of formula (III) in the presence of an oxidant and introduce carboxyl group to obtain (3R)-3-azido-4-(2,4,5-trifluorophenyl)-butyric acid of formula (IV).

The oxidant used in this reaction may be selected from the group consisting of NaIO₄, NaMnO₄, KMnO₄, H₂CrO₄, OsO₄, NaOCl, and a mixture thereof. In the reaction, the oxidant may be used in an amount of 1 to 5 equivalents based on the compound of formula (III).

Preferably, the step (iii) is preferably carried out in presence of a catalyst. The catalyst may be selected from the group consisting of RuCl₃, RuO₄, OsO₄, KMnO₄, and a mixture thereof. In the reaction, the catalyst may be used in an amount of 0.0001 to 0.1 equivalents based on the compound of formula (III).

In step (iv), (3R)-3-azido-4-(2,4,5-trifluorophenyl)-butyric acid of formula (IV) obtained in step (iii) is subjected to a condensation reaction with a triazol derivative of formula (VI) to obtain (3R)-3-azido-1-(3-trifluoromethyl)-5,6-dihydro-8H-[1,2,4]triazolo[4,3-a]pyrazin-7-yl)-4-(2,4,5-trifluorophenyl)-butan-1-one of formula (V).

Prior to the condensation reaction, (3R)-3-azido-4-(2,4,5-trifluorophenyl)-butyric acid of formula (IV) is treated with carboxyl group activator to activate the carboxyl group.

The carboxyl group activator may be selected from the group consisting of N-ethyl-N'-(3-dimethylaminopropyl)carbodiimide (EDC), N,N'-dicyclohexylcarbodiimide (DCC), 1,1'-carbonyldiimidazol (CDI), a mixture of DCC and 1-hydroxybenzotriazole (HOBt), a mixture of DCC and 1-hydroxysuccinimide, and a combination thereof.

In step (v), the azido group of compound of formula (V) obtained in step (iv) is reduced to obtain sitagliptin of formula (I).

In this reaction, the reductant may be a mixture of PPh₃ and H₂O, a mixture of PPh₃ and HCl, a mixture of PPh₃ and NH₄OH, a mixture of PPh₃ and H₂S, and the like. Also, the reductant may be hydrogen, HCOOH, (NH₄)O₂H, NH₂NH₂, BH₃, NaBH₄, a mixture of Zn and HCl, and a combination thereof, in the presence of a metallic catalyst such as Raney Ni, Pd, Pt, Pd/C, Pd/Al₂O₃, Pd(OH)₂/C, a combination thereof and the like.

In accordance with the method of the present invention, the high yield of sitagliptin can be prepared by a simple and a low cost method, which has not been achieved in the prior art.

Also, the present invention provides novel compounds, (2R)-1-(2,4,5-trifluorophenyl)-4-penten-2-ol of formula (II), (2S)-1-(2-azido-4-pentenyl)-2,4,5-trifluorobenzene of formula (III), (3R)-3-azido-4-(2,4,5-trifluorophenyl)-butyric acid of formula (IV) and (3R)-3-azido-1-(3-trifluoromethyl)-5,6-dihydro-8H-[1,2,4]triazolo[4,3-a]pyrazin-7-yl)-4-(2,4,5-trifluorophenyl)-butan-1-one of formula (V), which are the key intermediates used in the present invention.

The following Examples are intended to further illustrate the present invention without limiting its scope.

Preparation Example 1

Preparation of (2S)-2-(2,4,5-trifluorobenzyl)-oxirane

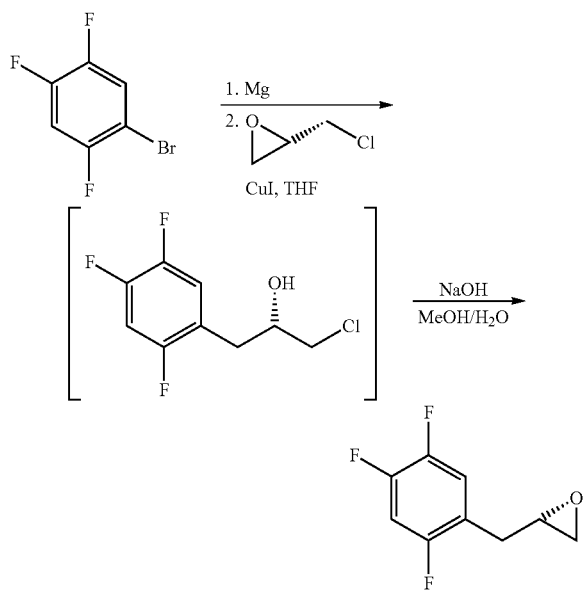

Step 1: Preparation of (2S)-3-(2,4,5-trifluorophenyl)-1-chloro-2-propanol

Magnesium (Mg) (1.26 g) was suspended in tetrahydrofuran (THF) (10 ml), and a drop of 1,2-dibromoethane was added thereto. To the resulting mixture, 2,4,5-trifluorobenzene bromide (0.55 g) was added dropwise slowly and then stirred for 30 min. 2,4,5-trifluorobenzene bromide (9.0 g) dissolved in THF (50 ml) was added slowly dropwise to the resulting mixture for 30 min and then stirred at room temperature for 1 hour. CuI (0.72 g) was added to the resulting mixture and the reaction temperature was cooled to 0° C. (S)-epichlorohydrin (4.1 ml) dissolved in THF (40 ml) was added dropwise to the resulting mixture slowly over 30 min, heated to room temperature, and stirred for 2 hours. Satuated NH$_4$Cl (50 ml) and ethyl acetate (50 ml) were added to the resulting mixture, and the organic layer formed thereafter was separated. The separated organic layer was washed with 50 ml of satuated saline, dried over MgSO$_4$, and filtered. The organic solvent was removed from the filtrate under a reduced pressure to obtain the title compound.

Step 2: Preparation of (2S)-2-(2,4,5-trifluorobenzyl)-oxirane (2S)-3-(2,4,5-trifluorophenyl)-1-chloro-2-propanol obtained in step 1 was dissolved in methanol (50 ml), and NaOH (2.3 g) was added dropwise thereto. The resulting mixture was stirred for 1 hour and methanol was removed therefrom under a reduced pressure. Water (50 ml) and ethyl acetate (50 ml) were added to the resulting mixture, and the organic layer formed thereafter was separated. The separated organic layer was washed with satuated saline, dried over MgSO$_4$, and filtered to remove MgSO$_4$. The organic solvent was removed from the filtrate under a reduced pressure to obtain the title compound (6.8 g; yield: 80%).

$^1$H-NMR (300 MHz, CDCl$_3$): δ 7.17-7.05 (2H, m), 6.96-6.88 (2H, m), 3.16-3.13 (1H, m) 3.14 (1H, dd, J=4.68, 14.7), 2.82-2.77 (2H, m), 2.54-2.47 (1H, m).

Preparation Example 2

Preparation of (2S)-2-(2,4,5-trifluorobenzyl)-oxirane

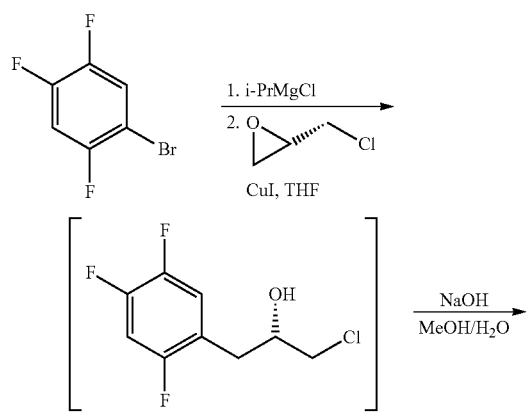

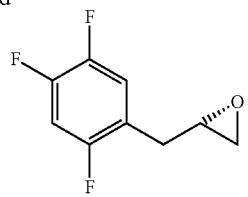

Step 1: Preparation of (2S)-3-(2,4,5-trifluorophenyl)-1-chloro-2-propanol 2N i-PrMgCl (26 ml) suspended in THF was added dripwise to the 2,4,5-trifluorobenzene bromide (9.55 g) dissolved in THF (30 ml) at −15° C. for 60 min. CuI (0.72 g) was added thereto at −15° C., and heated to −10° C. (S)-epichlorohydrin (4.1 ml) dissolved in THF (40 ml) was added slowly to the resulting mixture, and stirred at 0° C. for 1 hour. Satuated NH$_4$Cl (50 ml) and ethyl acetate (50 ml) were added to the resulting mixture, and the organic layer formed thereafter was separated. The separated organic layer was washed with 50 ml of satuated saline, dried over MgSO$_4$, and filtered to remove MgSO$_4$. The organic solvent was removed from the filtrate under a reduced pressure to obtain the title compound.

Step 2: Preparation of (2S)-2-(2,4,5-trifluorobenzyl)-oxirane (2S)-3-(2,4,5-trifluorophenyl)-1-chloro-2-propanol obtained in step 1 was dissolved in 50 ml of methanol, and NaOH (2.3 g) was added dropwise thereto. A mixture was stirred for 1 hour, and methanol was removed therefrom under a reduced pressure. Water (50 ml) and ethyl acetate (50 ml) were added thereto, and the organic layer formed thereafter was separated. The separated organic layer was washed with satuated saline, dried over MgSO$_4$, and filtered to remove MgSO$_4$. The organic solvent was removed from the filtrate under a reduced pressure to obtain the title compound (7.6 g; yield: 85%).

Example 1

Preparation of Sitagliptin

Step 1: Preparation of (2R)-1-(2,4,5-trifluorophenyl)-4-pentene-2-ol

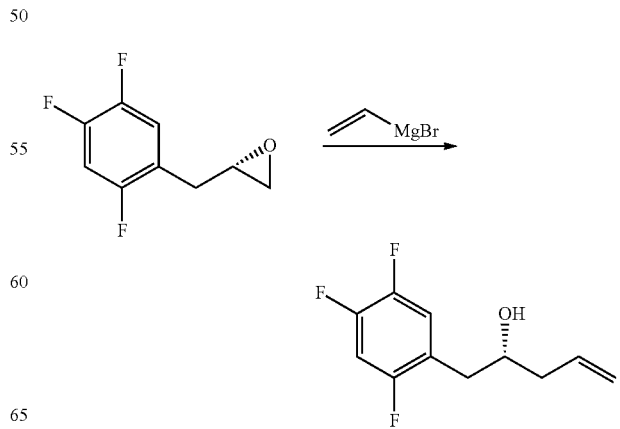

CuBr(CH$_3$)$_2$ (3.3 g) was added to a reactor under the nitrogen atmosphere and cooled to −78° C. Vinylmagnesium bromide (240 ml) was added slowly to the reactor and stirred for 20 min. (2S)-2-(2,4,5-trifluorobenzyl)-oxirane (30 g) dissolved in THF (90 ml) was added dropwise slowly over 30 min, stirred at −78° C. for 30 min, and heated to 0° C. 2N aqueous HCl (300 ml) was added slowly to the resulting mixture, and the organic layer formed thereafter was separated. The separated organic layer was washed twice with satuated saline, dried over MgSO$_4$, and filtered. The organic solvent was removed from the filtrate under a reduced pressure to obtain the title compound (34.5 g; yield: 100%).

$^1$H-NMR (300 MHz, CDCl$_3$): δ 7.15-7.06 (1H, m), 6.94-6.86 (1H, m), 5.85-5.79 (1H, m), 5.20-5.14 (2H, m), 3.90-3.85 (1H, m), 3.82 (1H, dd, J=4.6, 18.5), 2.69 (1H, dd, J=7.9, 14.0), 2.37-2.32 (1H, m), 2.24-2.17 (1H, m), 1.86 (1H, Br).

Step 2: Preparation of (2S)-1-(2-azido-4-pentenyl)-2,4,5-trifluorobenezene

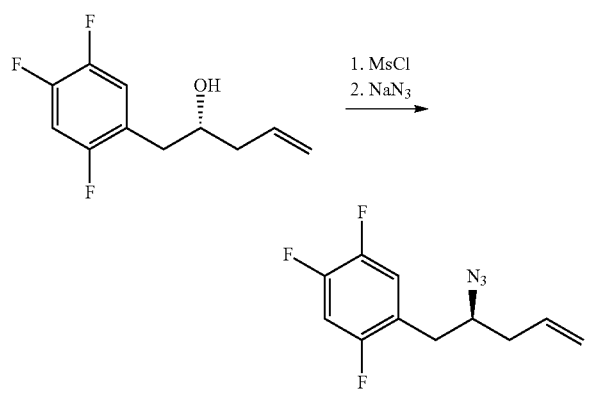

Dichloromethane (300 ml) was added to the (2R)-1-(2,4,5-trifluorophenyl)-4-pentene-2-ol obtained in step 1, and cooled to 0° C. Triethylamine (20.4 ml) and 4-dimethylaminopyridine (DMAP) (1.57 g) were added successively to the mixture, and methansulfonyl chloride (11.2 ml) was added dropwise thereto for 30 min. The resulting mixture was stirred for 1 hour, water (150 ml) was added, and the organic layer formed thereafter was separated. The separated organic layer was washed twice with satuated saline, dried over MgSO$_4$, and filtered. The organic solvent was removed from the filtrate under a reduced pressure. The residue thus obtained was dissolved in DMF (300 ml), and NaN$_3$ (9.91 g) was added thereto. The resulting mixture was heated to 70° C., stirred for 2 hours, and cooled to room temperature. And then water (150 ml) and ethyl acetate (150 ml) were added to the resulting mixture, and the organic layer formed thereafter was separated. The organic layer was washed twice with 150 ml of satuated saline, dried over MgSO$_4$, and filtered. The organic solvent was removed from the filtrate under a reduced pressure to obtain the title compound (31.5 g; yield: 94%).

$^1$H-NMR (300 MHz, CDCl$_3$): δ 7.11-7.02 (1H, m), 7.97-6.87 (1H, m), 5.89-5.80 (1H, m), 5.23-5.17 (1H, m), 3.63-3.59 (1H, m), 2.87 (1H, dd, J=4.7, 18.7), 2.68 (1H, dd, J=7.9, 13.7), 2.38-2.17 (2H, m).

Step 3: Preparation of (3R)-3-azido-4-(2,4,5-trifluorophenyl)-butyric acid

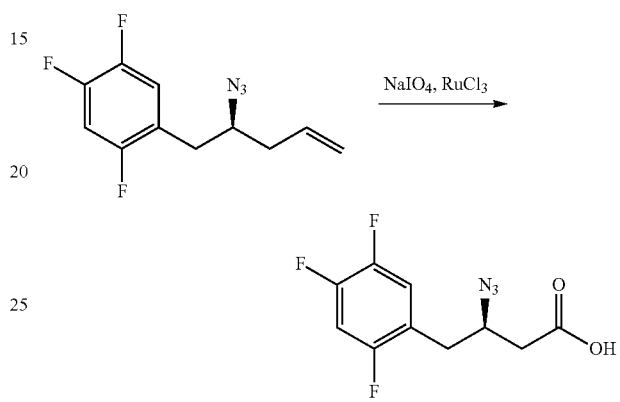

Acetonitril (300 ml) and water (300 ml) were added to the (2S)-1-(2-azido-4-pentenyl)-2,4,5-trifluorobenezene obtained in step 2, and cooled to 0° C. RuCl$_3$ (0.5 g) and NaIO$_4$ (93 g) were added to the mixture successively, and stirred for 5 hours. Ethyl acetate (90 ml) was added to the resulting mixture, filtered and the organic layer formed thereafter was separated. The separated organic layer was washed with 1N HCl (300 ml), satuated aqueous Na$_2$S$_2$O$_3$ (300 ml) and satuated saline (300 ml), successively, dried over MgSO$_4$, and filtered. The organic solvent was removed from the filtrate under a reduced pressure to obtain the title compound (32.2 g; yield: 100%).

$^1$H-NMR (300 MHz, CDCl$_3$): δ 10.5 (1H, br), 7.17-7.05 (1H, m), 7.02-6.87 (1H, m), 4.14-4.03 (1H, m), 2.94-2.78 (2H, m), 2.65-2.51 (2H, m).

Step 4: Preparation of (3R)-3-azido-1-(3-trifluoromethyl-5,6-dihydro-8H-[1,2,4]triazolo[4,3-c]pyrazin-7-yl)-4-(2,4,5-trifluorophenyl)-butan-1-one

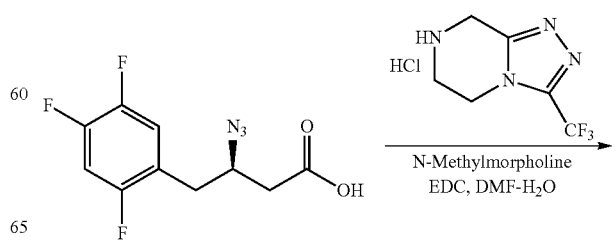

-continued

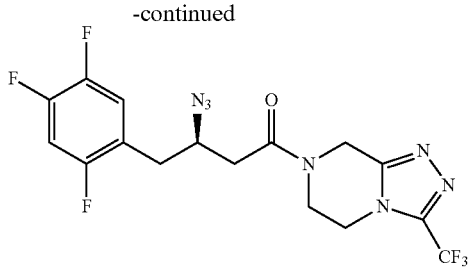

(3R)-3-azido-4-(2,4,5-trifluorophenyl)-buryric acid (5 g) obtained in step 3 and triazole derivative of formula (VI) (5.3 g) were added to DMF (40 ml) and water (20 ml), stirred for 15 min, and cooled to 10° C. N-methylmorpholine (2.4 ml) was added to the mixture, stirred for 10 min, and cooled to 0° C. EDC (5.6 g) was added to the resulting mixture, and stirred for 1 hour. Ethyl acetate (50 ml) and water (25 ml) were added to the resulting mixture, and the organic layer formed thereafter was separated. The separated organic layer was washed four times with 50 ml of satuated saline, dried over MgSO$_4$, and filtered. The organic solvent was removed from the filtrate under a reduced pressure to obtain the title compound (7.8 g; yield: 93%).

$^1$H-NMR (300 MHz, CDCl$_3$): δ 7.20-7.11 (1H, m), 6.99-6.90 (1H, m), 5.20-4.96 (2H, m), 4.28-4.05 (5H, m), 2.98-2.67 (4H, m).

Step 5: Preparation of sitagliptin

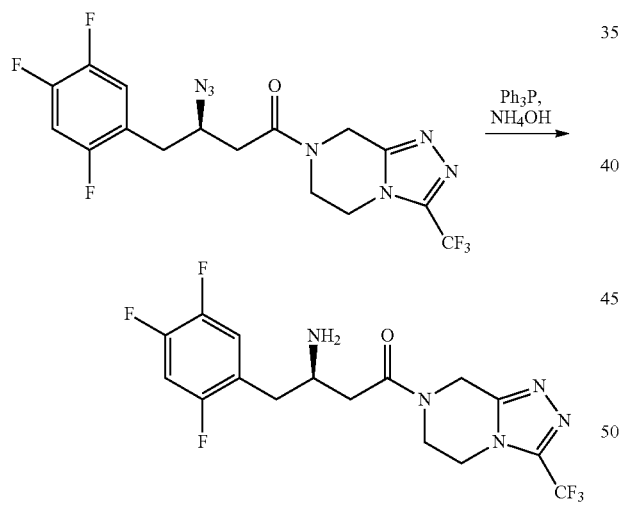

(3R)-3-azido-1-(3-trifluoromethyl-5,6-dihydro-8H-[1,2,4]triazolo[4,3-c]pyrazin-7-yl)-4-(2,4,5-trifluorophenyl)-butan-1-one (6.4 g) obtained in step 4 and triphenylphosphin (4.3 g) were dissolved in THF (74 ml), heated to 50° C., and stirred for 2 hours. An aqueous NH$_4$OH (37 ml) was added to the resulting mixture and stirred for 10 hours. THF was removed from the resulting mixture under a reduced pressure, HCl (30 ml) and ethyl acetate (60 ml) were added thereto, and stirred. The water layer separated from the mixture was washed twice with 30 ml of n-hexane, satuated sodium bicarbonate was added to the water layer, and extracted three times with 60 ml of ethyl acetate. The resulting extracts were dried over MgSO$_4$, and filtered. The organic solvent was removed from the filtrate under a reduced pressure to obtain the title compound (5.2 g; yield: 86%).

$^1$H-NMR (300 MHz, CDCl$_3$): δ 7.14-7.06 (1H, m), 7.00-6.88 (1H, m), 5.13-4.88 (2H, m), 4.24-3.80 (4H, m), 3.58 (1H, m), 2.85-2.66 (2H, m), 2.61-2.46 (2H, m), 2.11 (3H, br).

While the invention has been described with respect to the above specific embodiments, it should be recognized that various modifications and changes of the invention also fall within the scope of the present invention defined by the claims that follow.

What is claimed is:

1. A method of preparing sitagliptin of formula (I), which comprises the steps of:
   (i) allowing (S)-epichlorohydrin to undergo arylation, epoxidation, and vinylation reactions to obtain (2R)-1-(2,4,5-trifluorophenyl)-4-penten-2-ol of formula (II);
   (ii) azidatizing the compound of formula (II) to obtain (2S)-1-(2-azido-4-pentenyl)-2,4,5-trifluorobenzene of formula (III);
   (iii) oxidizing the compound of formula (III) to obtain (3R)-3-azido-4-(2,4,5-trifluorophenyl)-butyric acid of formula (IV);
   (iv) condensing the compound of formula (IV) with 3-(trifluoromethyl)-5,6,7,8-tetrahydro-[1,2,4]triazolo[4,3-a]pyrazine hydrochloride of formula (VI) to obtain (3R)-3-azido-1-(3-trifluoromethyl)-5,6-dihydro-8H-[1,2,4]triazolo[4,3-a]pyrazin-7-yl)-4-(2,4,5-trifluorophenyl)-butan-1-one of formula (V); and
   (v) reducing the azido group of (3R)-3-azido-1-(3-trifluoromethyl)-5,6-dihyrdro-8H-[1,2,4]-triazolo[4,3-a]pyrazin-7-yl)-4-(2,4,5-trifluorophenyl)-butan-1-one of formula (V) to obtain sitagliptin of formula (I):

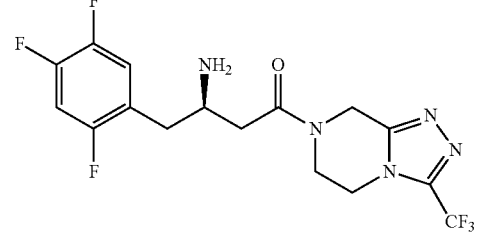
(I)

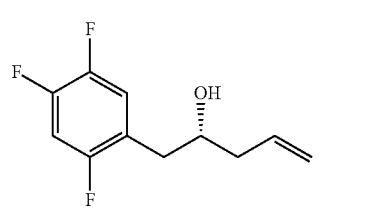
(II)

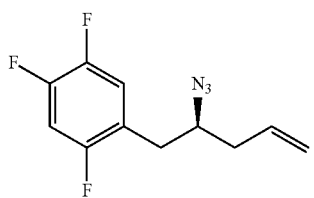
(III)

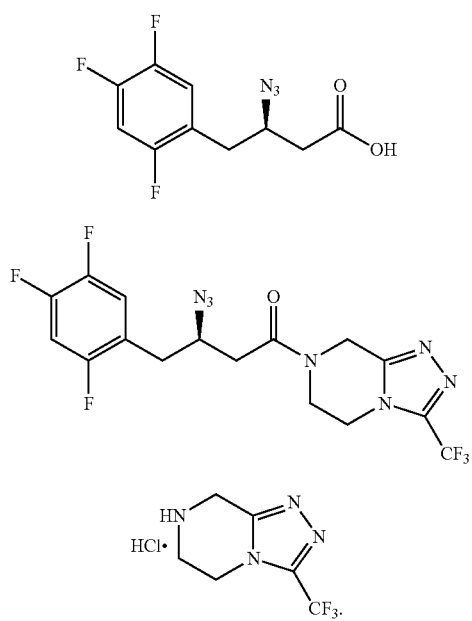

2. The method of claim 1, wherein step (ii) is conducted in the presence of an activator selected from the group consisting of mesyl chloride, p-tosyl chloride, benzenesulfonyl chloride, trifluoromethansulfonyl chloride, and a mixture thereof.

3. The method of claim 1, wherein the oxidant used in step (iii) is selected from the group consisting of $NaIO_4$, $NaMnO_4$, $KMnO_4$, $H_2CrO_4$, $OsO_4$, NaOCl, and a mixture thereof.

4. The method of claim 1, wherein step (iii) is conducted in the presence of a catalyst selected from the group consisting of $RuCl_3$, $RuO_4$, $OsO_4$, $KMnO_4$, and a mixture thereof.

5. The method of claim 1, wherein step (v) is conducted using a reductant selected from the group consisting of a mixture of $PPh_3$ and $H_2O$, a mixture of $PPh_3$ and HCl, a mixture of $PPh_3$ and $NH_4OH$, and a mixture of $PPh_3$ and $H_2S$.

6. The method of claim 1, wherein step (v) is conducted using a reductant selected from the group consisting of hydrogen, HCOOH, $NH_4OH$, $NH_2NH_2$, $BH_3$, $NaBH_4$, a mixture of Zn and HCl, and a combination thereof, in the presence of a metallic catalyst selected from the group consisting of Raney Ni, Pd, Pt, Pd/C, $Pd/Al_2O_3$, $Pd(OH)_2/C$, and a mixture thereof.

* * * * *